US007357817B2

(12) United States Patent
D'Alessio, II

(10) Patent No.: US 7,357,817 B2
(45) Date of Patent: Apr. 15, 2008

(54) MODULAR KEEL TIBIAL COMPONENT

(75) Inventor: Jerry D'Alessio, II, Belleville, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 384 days.

(21) Appl. No.: 11/133,014

(22) Filed: May 19, 2005

(65) Prior Publication Data
US 2006/0265079 A1  Nov. 23, 2006

(51) Int. Cl.
A61F 2/38 (2006.01)
(52) U.S. Cl. ............... 623/20.15; 623/20.34; 623/20.14; 623/20.33
(58) Field of Classification Search ............. 623/20.14, 623/20.15, 20.21, 20.22, 20.28, 20.29, 20.32–20.34
See application file for complete search history.

(56) References Cited

U.S. PATENT DOCUMENTS

| 4,834,081 A | * | 5/1989 | Van Zile ................ 128/92 |
| 4,923,472 A | | 5/1990 | Ugolini |
| 4,936,847 A | | 6/1990 | Manginelli |
| 4,936,853 A | | 6/1990 | Fabian et al. |
| 4,938,769 A | | 7/1990 | Shaw |
| 4,944,756 A | | 7/1990 | Kenna |
| 4,944,757 A | * | 7/1990 | Martinez et al. ........ 623/20.15 |
| 5,152,796 A | | 10/1992 | Slamin |
| 5,152,797 A | | 10/1992 | Luckman et al. |
| 5,326,359 A | | 7/1994 | Oudard |
| 5,413,605 A | | 5/1995 | Ashby et al. |
| 5,556,433 A | | 9/1996 | Gabriel et al. |
| 5,879,394 A | | 3/1999 | Ashby et al. |
| 5,928,286 A | | 7/1999 | Ashby et al. |
| 6,258,127 B1 | | 7/2001 | Schmotzer |
| 6,299,645 B1 | | 10/2001 | Ogden |
| 6,506,216 B1 | | 1/2003 | McCue et al. |
| 6,620,198 B2 | | 9/2003 | Burstein et al. |
| 6,719,800 B2 | | 4/2004 | Meyers et al. |

(Continued)

OTHER PUBLICATIONS

Product Information, Stryker Howmedica, Take a Step Closer to Natural Motion, InteraxlSA . . . a step closer to natural motion.

(Continued)

Primary Examiner—Brian D Nash
Assistant Examiner—Benjamin P Rice
(74) Attorney, Agent, or Firm—Lerner, David, Littenberg, Krumholz & Mentlik, LLP

(57) ABSTRACT

A modular keel or stem for use as a tibial implant has a central stem portion including a coupling portion for insertion into and through an opening in a tibial baseplate. The modular keel or stem may also include a pair of anti-rotation fins or ribs which extend medially and posteriorly on the medial side and laterally-posteriorly on the lateral side for engaging receptacles in the bone contacting of the tibial baseplate. A locking element is provided for engaging the keel or stem coupling portion and the baseplate after the coupling portion of the keel is inserted through the opening to prevent the disassembly the keel from the baseplate. The coupling element is capable of being inserted in a medial-lateral direction after the keel and baseplate have been implanted. A polymeric bearing insert is provided for placement on the baseplate which insert includes a recess or opening for receiving the coupling element.

16 Claims, 7 Drawing Sheets

U.S. PATENT DOCUMENTS

| | | |
|---|---|---|
| 6,866,683 B2 | 3/2005 | Gerbec et al. |
| 6,887,267 B2 | 5/2005 | Dworschak et al. |
| 2003/0158606 A1 | 8/2003 | Coon et al. |
| 2003/0171757 A1 | 9/2003 | Coon et al. |
| 2003/0204263 A1 | 10/2003 | Justin et al. |
| 2004/0073315 A1 | 4/2004 | Justin et al. |
| 2004/0102852 A1 | 5/2004 | Johnson et al. |
| 2004/0117023 A1 | 6/2004 | Gerbec et al. |
| 2004/0117024 A1 | 6/2004 | Gerbec et al. |
| 2004/0225368 A1* | 11/2004 | Plumet et al. ............ 623/20.15 |
| 2005/0102031 A1* | 5/2005 | Leonard ................... 623/20.21 |
| 2006/0195196 A1* | 8/2006 | Pendleton et al. ........ 623/20.34 |

OTHER PUBLICATIONS

U.S. Appl. No. 11/177,087, Collazo.

* cited by examiner

MODULAR KEEL TIBIAL COMPONENT

BACKGROUND OF THE INVENTION

This invention relates to a modular tibial component for use in total knee arthroplasty. More particularly, it relates to a modular tibial component for use in Minimally Invasive Surgery (MIS) wherein all the modular tibial components can be installed through an incision on either the medial side or lateral side or on an anterior-lateral or anterior-medial location on the knee.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

In the past, resurfacing of a knee joint was performed with the implantation of prosthetic femoral and tibial components through an incision extending proximally to distally along the anterior surface of the knee adjacent the lateral or medial sides of the patella. This required a comparatively long incision to be made in order to install the prosthetic femoral and tibial component. Recently, there has been progress towards shortening the incision and moving the incision either medially or laterally from the prior art anterior incision. While direct medial or lateral approaches are possible, it is preferred to have an anterior-medial or anterior-lateral approach.

U.S. Patent Publication No. 2003/0171757 relates to such a minimally invasive total knee arthroplasty method and instrumentation used therefor. In addition, in co-pending U.S. application Ser. No. 10/768,520 assigned to the assignee of the present invention discloses instrumentation for use with such a minimally invasive method.

Incisions size, while of secondary importance to not everting or subluxing the patella, has been reduced and may be in the range of 7-9 cm. Consequently it has been found necessary to utilize femoral and tibial prosthetic implants which are adapted to be inserted through this reduced incision. One way of producing such an implant is to make the typical parts of the implant modular so that they may be inserted into a prepared knee in series. For example, with respect to the tibia, a typical tibial implant includes a stem or a keel, a baseplate and a modular bearing insert typically made of a polymeric material such as ultra-high molecular weight polyethylene.

In the present invention, the stem or keel has been made a separate element from the tibial baseplate which supports the polymeric bearing component with the stem or keel including a coupling feature which can be inserted through an aperture in the baseplate or in the locking element which can preferably be inserted in the medial to lateral or lateral to medial direction is used to lock the coupling feature of the keel to the baseplate and the polymeric bearing insert includes a recess, which can be in the form of an opening, to receive the locking element and the keel coupling element so that these elements are either captured within the polymeric bearing insert or at least do not extend proximally into contact with the femoral component. The same could be accomplished by using a two piece polymeric bearing component having a separate lateral condylar component and medial condylar component with a space in between for receiving the locking element. Of course if an anterior incision is used the locking or coupling element can be inserted in the anterior to posterior direction.

Modular prosthetic knee components are known and are shown in U.S. Pat. No. 5,152,796, U.S. Pat. No. 5,326,359, U.S. Pat. No. 6,258,127, U.S. Pat. No. 6,506,216, and U.S. Pat. No. 5,413,605. These patents relate to methods of attaching modular stems or keels to a femoral or tibial component.

The use of dovetails is also known in prosthetic knee implant applications and such are shown in U.S. Pat. Nos. 4,923,472 and 6,299,645.

SUMMARY OF THE INVENTION

It is one aspect of the invention to provide a modular tibial component with parts which can be inserted into a prepared proximal tibia in series.

It is yet another aspect of the invention to provide a tibial component having a modular keel or stem which can be coupled to a modular tibial baseplate and locked thereto by use of a locking element insertable in the medial to lateral or lateral to medial direction.

It is still a further aspect of the invention to provide a modular polymeric bearing which can be inserted and locked to the tibial baseplate which bearing includes a recess or opening for receiving the locking element as well as the proximal portion of the modular keel or stem.

These and other aspects of the invention are disclosed in a modular tibial implant comprising a tibial baseplate having a medial side, lateral side with a plate having a bone contacting surface and a superior surface extending between the medial and lateral sides of the baseplate. The plate includes an opening or aperture therein preferably centrally located between the medial and lateral sides.

A modular keel is provided, which keel has a central stem portion including a coupling portion for insertion into and through the opening and plate. The modular keel may also include a pair of anti-rotation fins which extend medially and posteriorly on the medial side and laterally-posteriorly on the lateral side of the tibial baseplate. A coupling element is provided for engaging the keel coupling portion and the baseplate after the coupling portion of the keel is inserted through the aperture to prevent the disassembly thereof. The coupling element is capable of being inserted preferably in a medial to lateral or lateral to medial direction after the keel and baseplate have been implanted. A polymeric bearing insert is provided for placement on the baseplate which insert includes a recess or opening for receiving the coupling element after it engages the keel. The coupling system could be oriented and the locking or coupling element inserted at about 45° to the medial-lateral direction towards the anterior or even directly anterior depending on where the incision is made in the knee.

Preferably, the coupling portion on the keel has a dovetail shape with the dovetail having a pair of inwardly angled planar surfaces capable of being oriented in a medial-lateral direction. Likewise, the coupling or locking element has a dovetail with a pair of angled surfaces for capturing the pair of angled surfaces on the coupling portion dovetail and also includes a surface for engaging a superior surface of the plate.

On a portion of the keel below the baseplate after assembly, the keel includes a first fin extending radially outwardly from the stem portion at a posterior angle to the medial direction and a second fin extending radially outwardly of the stem at a posterior angle to the lateral direction. In general, the fin preferably extends at about a 30 degree angle from a medial-lateral plane posteriorly on both sides, thus forming a V-shape. The inferior or bone contacting surface of the tibial baseplate includes a pair of inferiorly extending receptacles for receiving proximal end portions of each of the first and second fins. In one embodiment, the proximal surfaces of the fins are inwardly tapered and match an inward taper on the receptacles. Thus, the fins may engage the receptacles and form a friction lock therein by engagement of the tapered surfaces. Preferably, each receptacle has the female tapered portion and the fins on the keel have the male tapered portion. In a preferred embodiment, the proximal fins are straight walls which engage straight walls or recesses in the keel.

While a dovetail connection has been described, for the coupling element, any locking system such as a spring clip or tongue and groove could be used as long as it can be introduced in a plane generally parallel to the plane of the resected proximal tibia. In addition, the coupling element such as the dovetail connection could be used on a stem without fins such as a typical modular cylindrical stem.

The polymeric insert has an inferior surface which engages the superior surface of the baseplate. The insert has a recess in the inferior surface thereof or an opening sized to receive the coupling element or locking element upon placement of the insert into the baseplate. The insert is locked into the baseplate in any manner well known in the art.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

Figure 1:
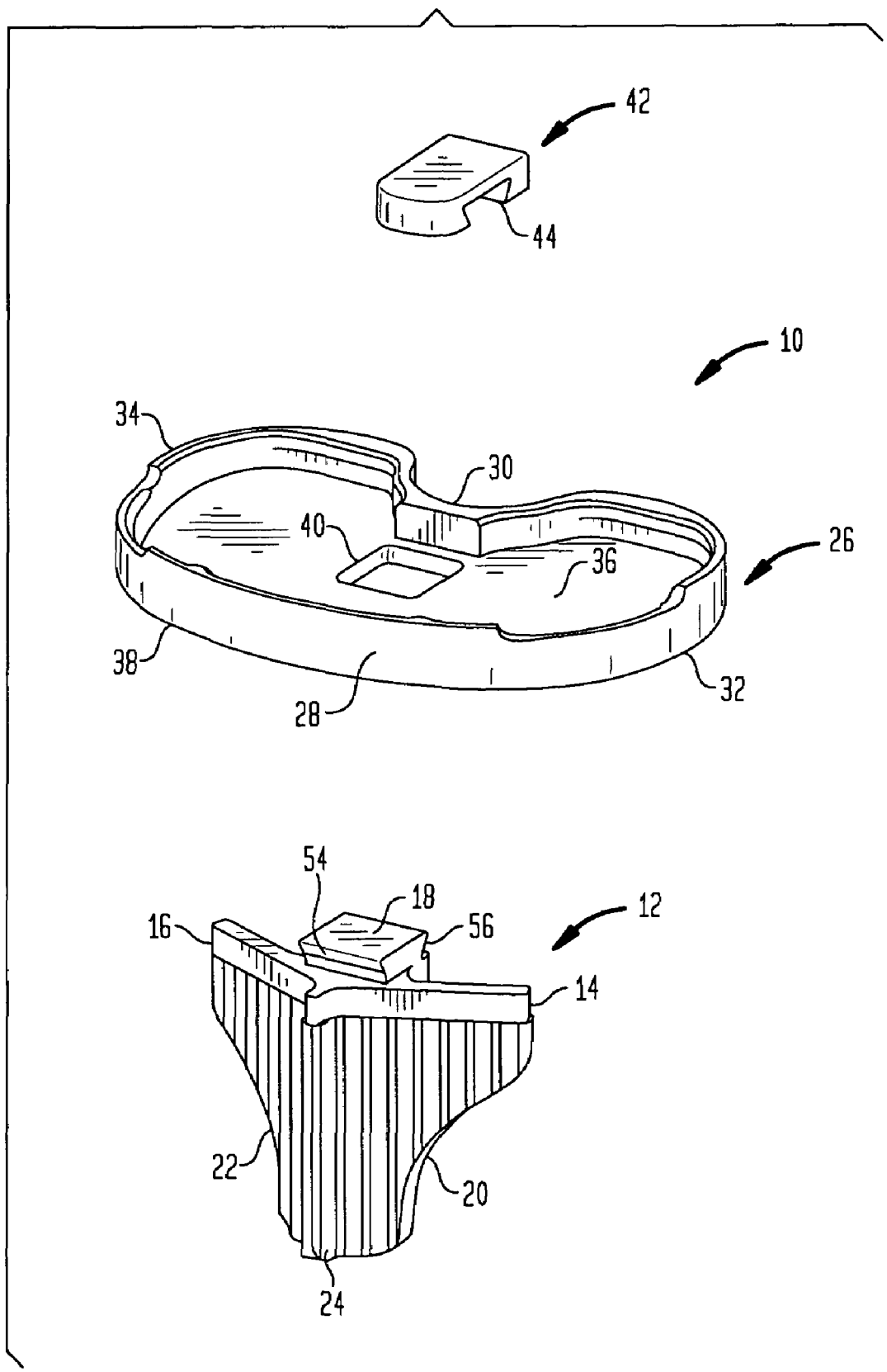
FIG. 1 is an exploded perspective view of the modular tibial keel, baseplate and coupling element of the present invention.

Referring to FIG. 1, there is shown an exploded view of the tibial tray assembly of the present invention generally denoted as 10. A modular polymeric bearing insert is also utilized in the system but is not shown in FIG. 1. The modular tibial implant 10 consists of a modular keel 12 having a pair of fins 14 and 16 and an integral coupling element 18 extending proximally from the central portion of the keel 12. The preferred fins 14 and 16 are tapered inwardly towards the central axis of the keel at points 20 and 22 on moving from the proximal end of the keel which includes coupling element 18 to distal end 24.

Assembly 10 also includes a baseplate 26 having an anterior side 28, a posterior side 30 and medial or lateral sides 32 and 34. As is typical, posterior side 30 includes a notch for the posterior collateral ligament. A baseplate has a superiorly facing surface 36 and a bone contacting surface 38 with an aperture 40 extending between surfaces 36 and 38 preferably along the anterior-posterior centerline of the baseplate. A locking element 42 is also provided which has an inwardly tapered female dovetail section 44 for receiving a male dovetail section 54, 56 of coupling element 18. The coupling element could also be in the form of a T-shaped slot, a reverse dovetail or a ball and socket joint.

Figure 2:
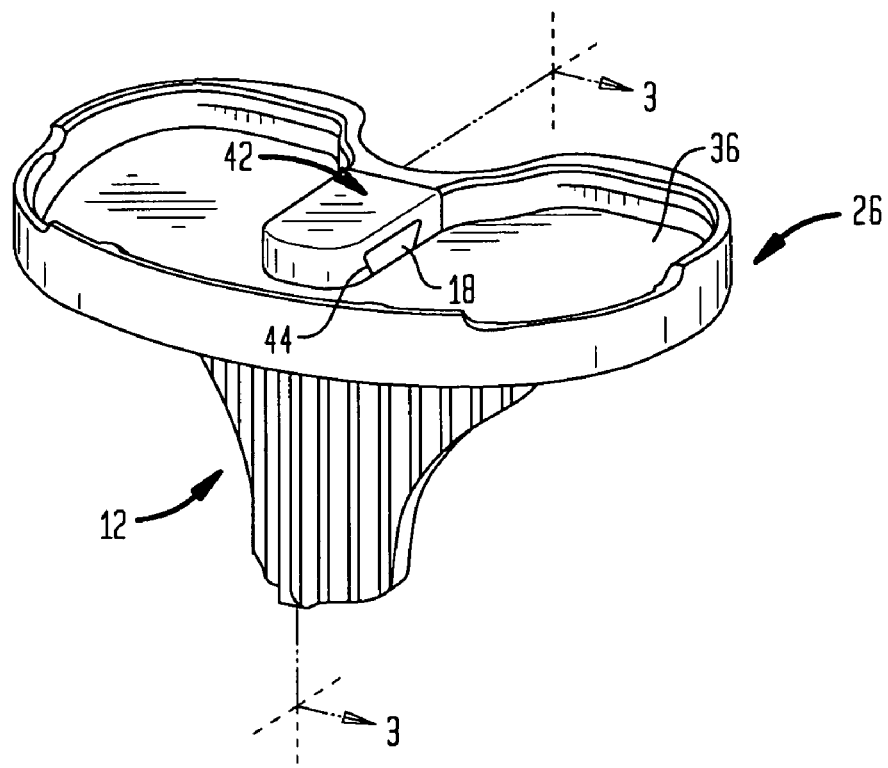
FIG. 2 is a perspective view of the assembled keel, baseplate and coupling element of FIG. 1.
Figure 3:
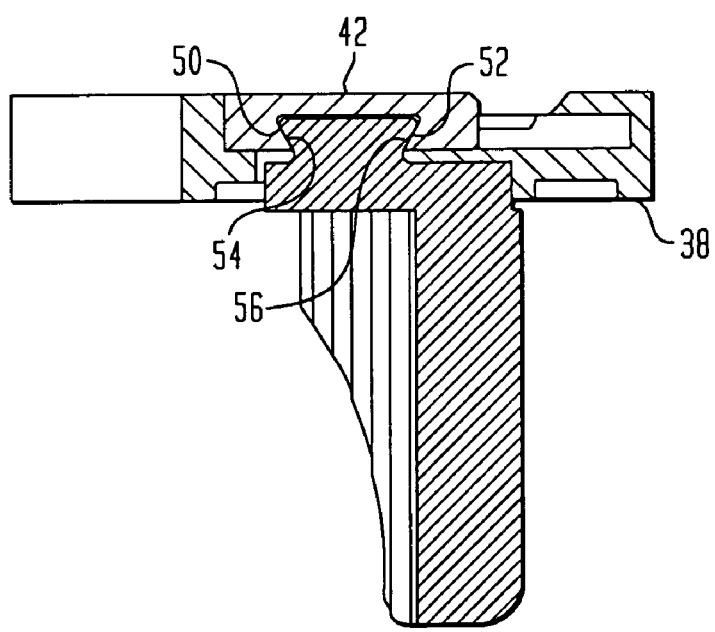
FIG. 3 is a cross-sectional view of the assembly of FIG. 2 along lines 3-3.

Referring to FIGS. 2 and 3, there is shown the modular tibial implant assembly 10 of the present invention in the assembled condition. It can be seen that keel 12 is held onto baseplate 26 by the engagement of dovetail 44 with the dovetail of keel 18 after the same has been inserted through aperture 40 in baseplate 26 thereby locking the assembly together. It can be seen that the angled surfaces 50 and 52 of dovetail 44 are oriented in the medial-lateral direction and engage the complementary dovetail surfaces 54 and 56 of coupling element 18 of keel 12. It can be seen that when the complementary dovetails are aligned in the medial-lateral direction, locking element 42 can be easily slide on superior surface 36 of baseplate 26 into engagement with coupling element 18. Preferably, aperture 40 is polygonal in shape, such as square, which aligns with a complimentary surface 57 on coupling element 18.

Figure 4:
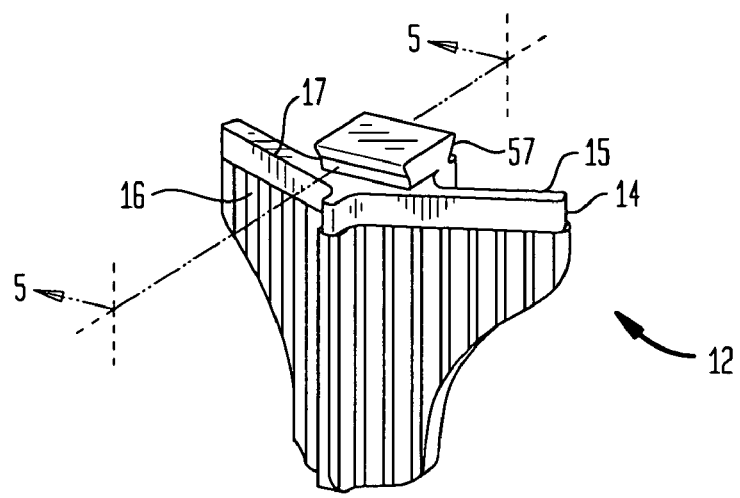
FIG. 4 is a perspective view of the keel element of the present invention.
Figure 5:
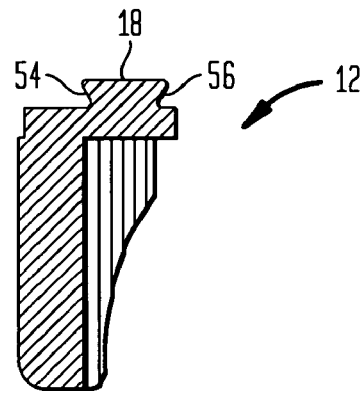
FIG. 5 is a cross-sectional view of the keel shown in FIG. 4 along lines 5-5.
Figure 6:
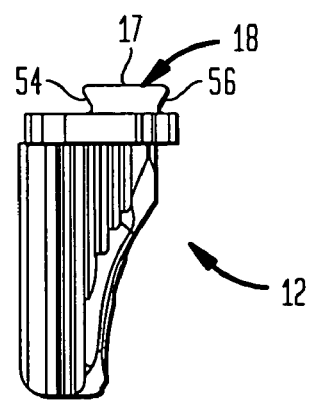
FIG. 6 is a side view of the modular keel of FIG. 4.

Referring to FIGS. 4 through 6, various views of keel 12 are shown. Referring to FIG. 4, fins 14 and 16 are shown which may be preferably inwardly tapered for engagement with a receptacle on the baseplate inferior surface as will be discussed below.

Figure 7:
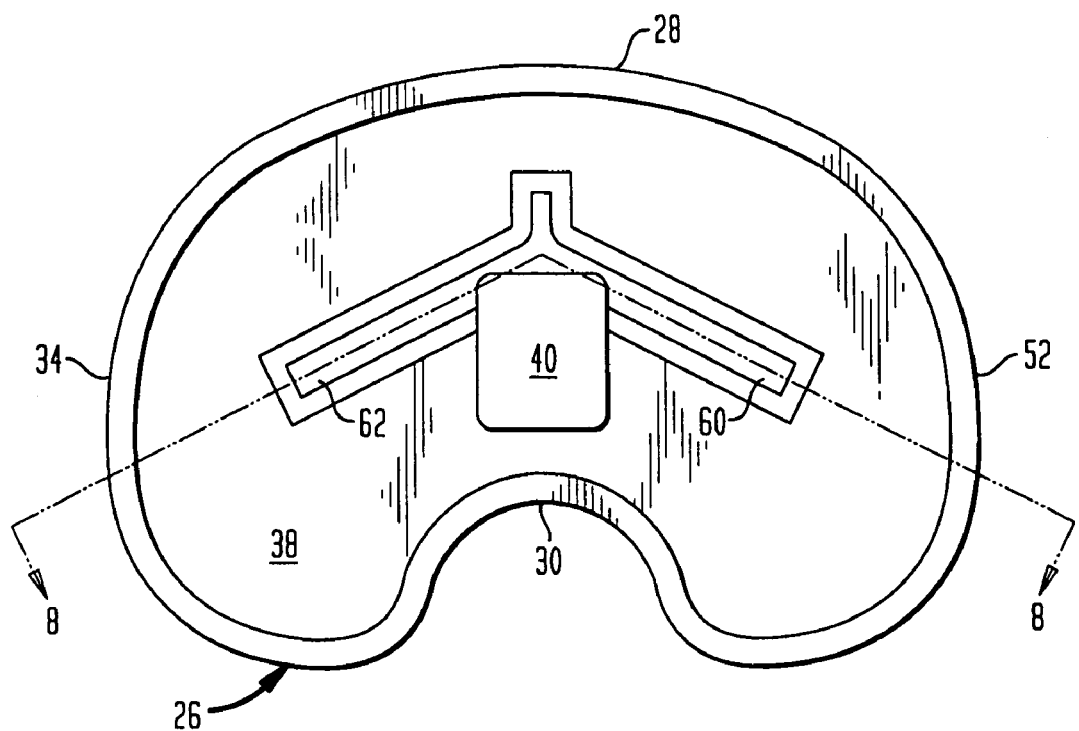
FIG. 7 is a bottom view of the tibial baseplate of the present invention.
Figure 8:
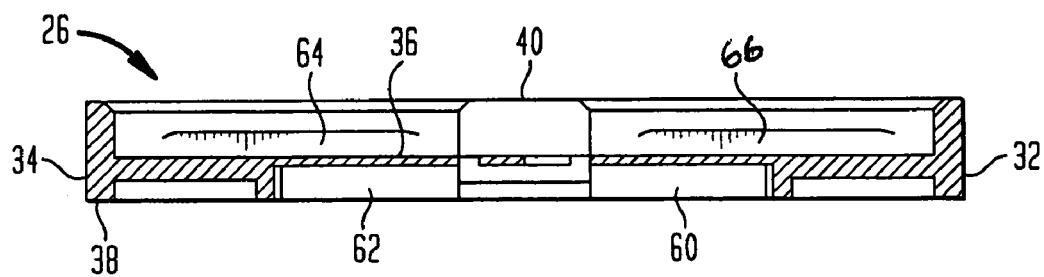
FIG. 8 is a cross-sectional view of the baseplate of FIG. 7 along lines 8-8.

Referring to FIGS. 7 and 8, there is shown the baseplate 26 including aperture 40 as well as a V-shaped receptacle 60 and 62 respectively located on the medial and lateral sides of the inferior baseplate surface 38. Slots 60 and 62 are sized to receive the proximal edges 15 and 17 of fins 14 and 16. As discussed above, the proximal portions 15 and 17 of fins 14 and 16 may be inwardly tapered and thus it is possible to inwardly taper the receptacles 60 and 62 in a complementary manner to receive the portions 15 and 17 and form a taper lock therebetween.

Since the main purpose of the engagement of the fins on the baseplate receptacles is to prevent rotation of the keel, the fins and receptacles could be rectangular in shape and not tapered. The engagement is also for load sharing and transfer from the baseplate through the keel, although not optimal for such load transfer.

Referring to FIG. 8, there is shown a cross-sectional view which includes the superior surface 36 of baseplate 26 which includes a pair of locking features 64 and 66 which are adapted to lockingly engage the polymeric bearing insert.

The proximal tibia is prepared in the normal minimally invasive fashion for all bone cuts including punching the keel. This includes forming a planar surface on the proximal tibia. The tibial keel is inserted first, into the prepared tibia. Additionally, in a press-fit cementless situation, the actual tibial keel implant can be used as the tibial punch reducing a surgical step. In addition, using the keel provides an excellent fit since the keel punch is not removed which may widen the fin area. The tibial baseplate would then be placed over the keel, and the superior portion of the keel lined up with the inferior recess on the tibial plate. The locking element would then be installed by moving it generally parallel or at a small angle to the plane of the prepared proximal tibia locking the tibial tray and keel together onto the tibial baseplate. The locking element may be slid in a medial-lateral or anterior-medial or lateral direction along a plane generally parallel or at a small angle to the baseplate plane. Final impacting of the assembled components can be performed if necessary. The polymeric bearing can then be installed.

Although the present invention is primarily useful for the insertion of the tibia in MIS situations, it would make revision of such an implanted modular tray more simple and versatile. The tray alone can be removed and replaced if the keel is well fixed. If a well fixed keel needs to be removed, the tray can be taken off separately and a keel chisel can be used to separate the bone from around the keel. Currently one piece tibial trays are cut with a power instrument to access the keel causing metal debris and heat as adverse effects for the patient.

Figure 9:
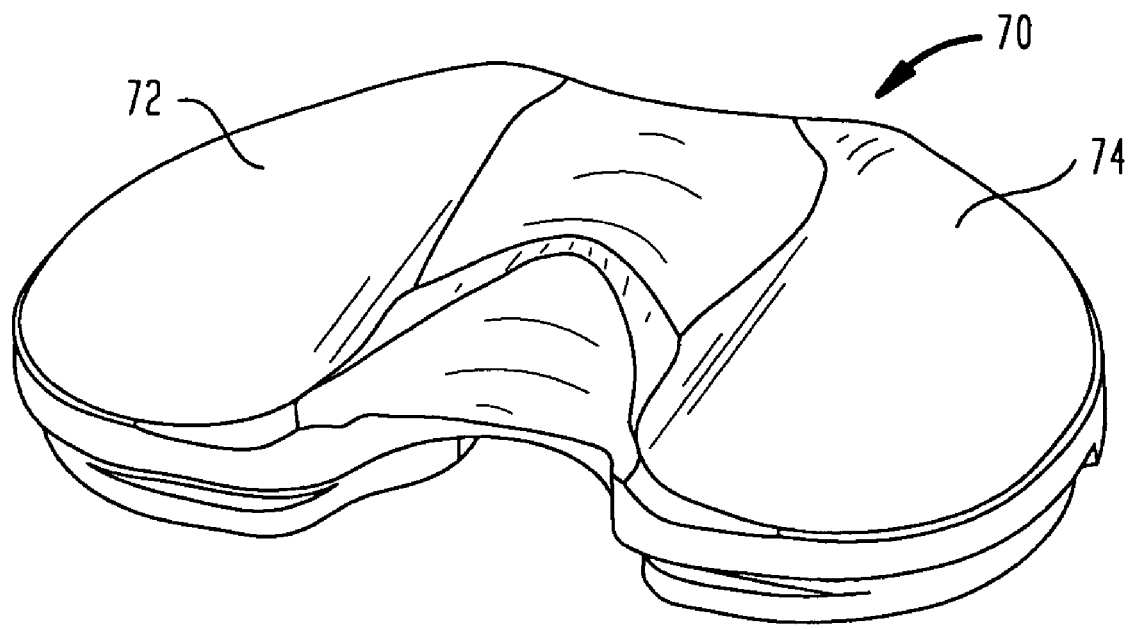
FIG. 9 is a top rear isometric view of the polymeric bearing insert for use with the modular keel of FIG. 1.
Figure 10:
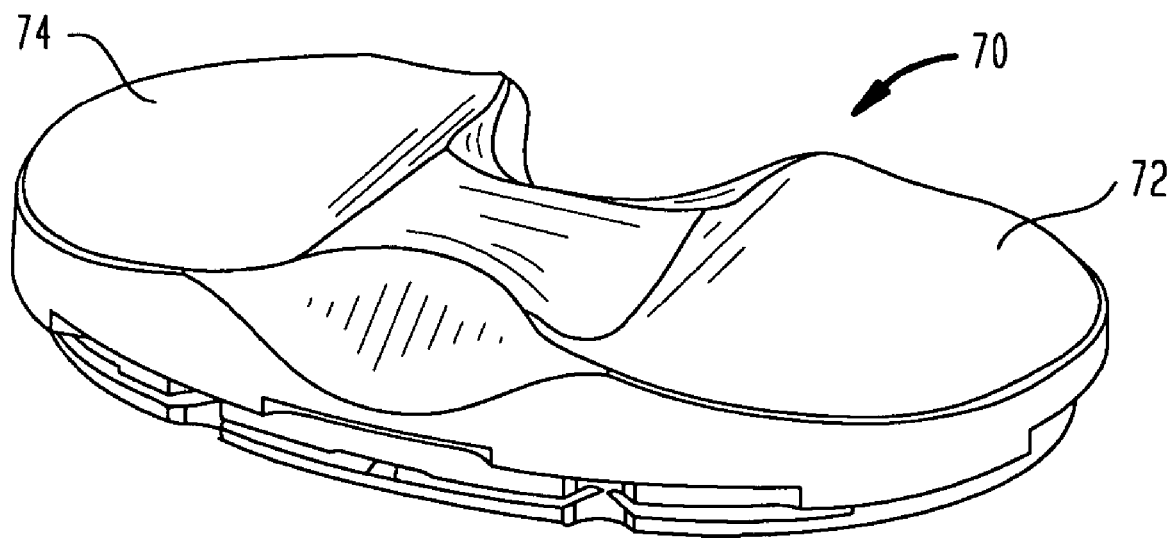
FIG. 10 is a top front isometric view of a polymeric bearing component for use with the baseplate of the present invention.
Figure 11:
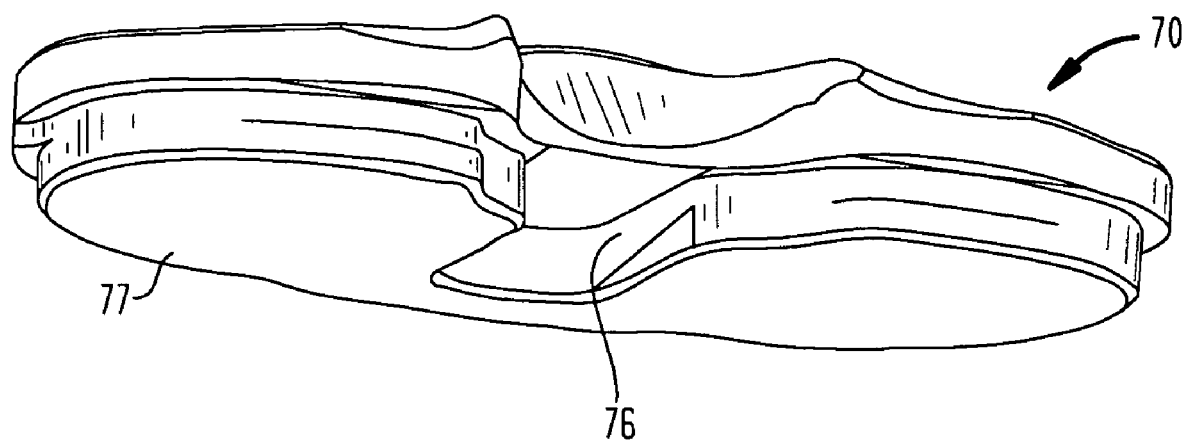
FIG. 11 is a bottom isometric view of the polymeric bearing component of FIG. 10.

Referring to FIGS. 9 to 11, there is shown the polymeric bearing insert generally denoted as 70 which includes a pair of bearing surfaces 72 and 74 on a superior side thereof and includes recess 76 on an inferior side 77 thereof. The inferior surface recess 76 is sized to receive coupling element 18 and locking element 42 mounted thereon such that when element 42 is received in the recess, it cannot slide in a medial-lateral direction to disengage from the coupling element 18. In all other respects, bearing insert 70 is similar to those utilized in the prior art and includes locking features 64 and 66 which engage complementary locking features 64', 66' on the tibial baseplate 26 which are also well known. The engagement of the complementary features on the bearing insert 70 ensures that the bearing element does not disengage from baseplate 26 during use.

Figure 12:
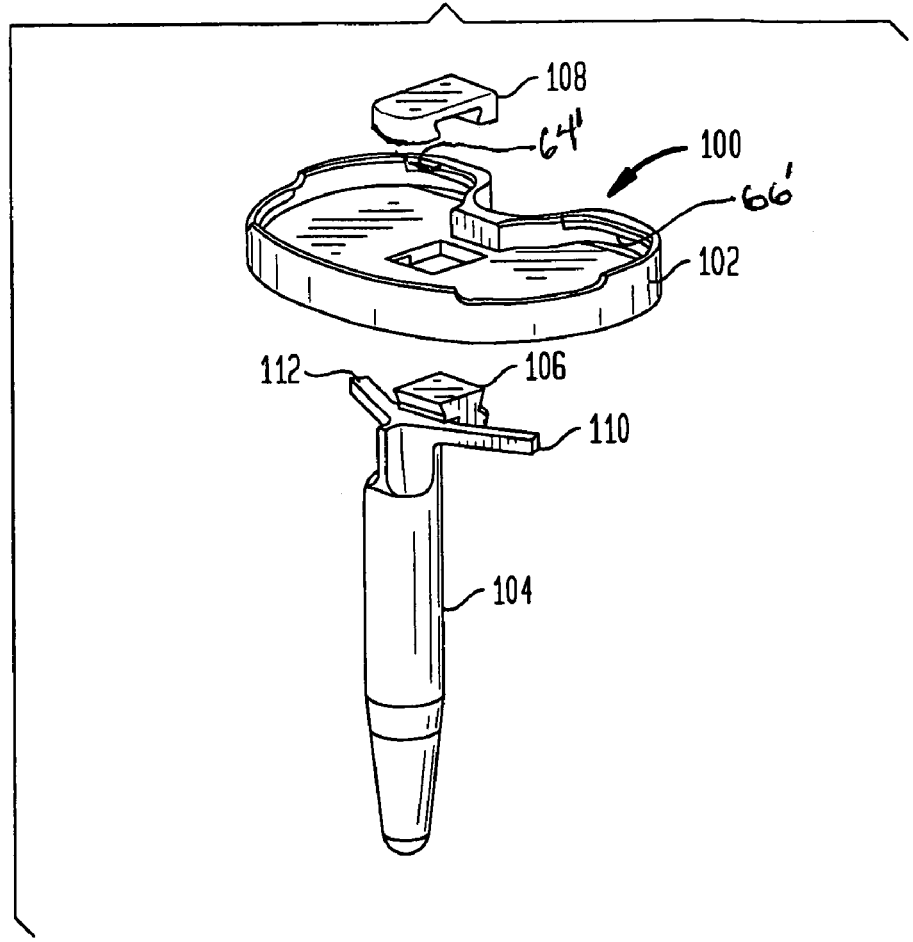
FIG. 12 is an exploded isometric view of a second embodiment of the present invention.
Figure 13:
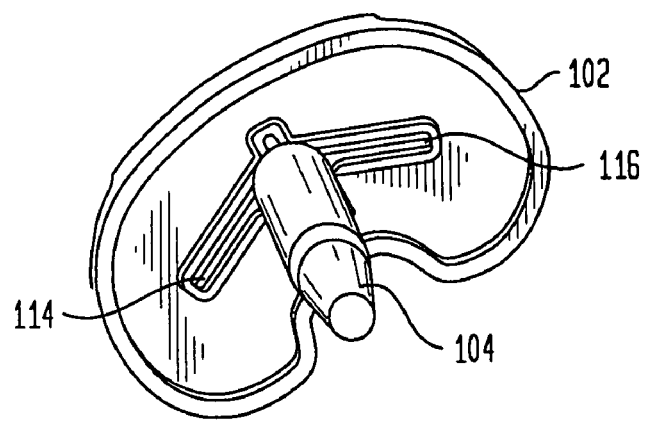
FIG. 13 is a bottom view of the assembled stem and baseplate shown in FIG. 12.

Referring to FIGS. 12 and 13 there is shown an alternate embodiment where the tibial implant 100 has a tibial baseplate or tray 102 and a modular stem 104 rather than a modular finned keel 12 as used in the preferred embodiment. Stem 104 includes the same or a similar coupling element 106 as coupling element 18 used on finned keel 12. Likewise, the locking element 108 may be the same or similar to locking element 42. The proximal end of stem 104 includes generally medial-laterally extending anti-rotation ribs 110 and 112 which are similar to the proximal part of fins 14 and 16 and engage grooves 114 and 116 in the bone contacting side of baseplate 102. As with fins 14 and 16 ribs 110 and 112 help prevent the rotation of the stem 104 with respect to the baseplate as well as helping to distribute the load on the baseplate to the stem. The same bearing insert 70 is used as on the preferred embodiment.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A modular tibial implant comprising:
 a tibial baseplate having a medial side, a lateral side an anterior side and a posterior side with a plate having a bone contacting surface and a superior surface extending between said sides of said plate, said plate including an opening therein;
 a modular bone engagement element in the form of a keel or stem having a distal bone engaging portion and a proximal coupling portion for insertion into and through said opening in said plate wherein said proximal coupling portion on said keel or stem has a dovetail shape, the dovetail having a pair of angled surfaces capable of being oriented in a medial-lateral direction;
 a coupling element for engaging said proximal coupling portion of said bone engagement element after the bone engaging element has been inserted through said opening to prevent disassembly thereof, said coupling element capable of being inserted in a direction offset from the anterior-posterior direction after said bone engaging element and baseplate have been implanted; and
 a polymeric bearing insert for placement on said baseplate having a recess for receiving said coupling element.

2. The modular tibial implant as set forth in claim 1 wherein said coupling element has a pair of angled surfaces for capturing, said pair of angled surfaces on said coupling portion dovetail and a surface for engaging said superior surface of said bone plate.

3. The modular tibial implant as set forth in claim 1 wherein said keel includes a first fin extending radially outwardly from said stem portion at an angle to said medial side of said baseplate and a second fin extending radially outwardly of said stem at an angle to said lateral side of said baseplate.

4. The modular tibial implant as set forth in claim 3 wherein said baseplate bone contacting surfaces include a pair of inferiorly extending receptacles for receiving a proximal end portion of each of said first and second fins.

5. The modular tibial implant as set forth in claim 4 wherein each receptacle has a female tapered portion for engaging a male tapered portion on said first and second fin proximal end portions.

6. The modular tibial implant as set forth in claim 1 wherein said polymeric insert for placement on said baseplate superior surface having a superior bearing surface and an inferior surface for engaging the superior surface of said baseplate and having a recess in said inferior surface thereof sized to receive said proximal coupling element upon placement of said insert on said baseplate.

7. The modular tibial implant as set forth in claim 1 wherein the coupling element is inserted in a generally anterior-medial or anterior-lateral direction.

8. A modular tibial baseplate comprising:
 a tibial baseplate having an opening therein;
 a modular bone engaging element having a stem portion at a first end and a coupling portion at a second end, said coupling portion receivable in said opening in said baseplate, with a portion of said coupling portion extending beyond a superiorly facing surface of said baseplate; and
 means for coupling said bone engaging element to said baseplate including means for locking said bone engaging element coupling portion to said baseplate wherein said locking means includes a dovetail joint and wherein said coupling portion on said bone engaging element has a dovetail shape, the dovetail having a pair of inwardly angled surfaces oriented in a medial-lateral direction upon assembly with said baseplate.

9. The modular tibial implant as set forth in claim 8 wherein said means for coupling said bone engaging element to said baseplate is a coupling element having a pair of angled surfaces for capturing said pair of angled surfaces on said coupling portion dovetail and a surface for engaging a superior surface of said bone plate.

10. The modular tibial implant as set forth in claim 8 wherein said bone engaging element includes a first fin extending radially outwardly from said stem portion at an angle to said medial direction and said second fin extending radially outwardly of said stem at an angle to said lateral direction.

11. The modular tibial implant as set forth in claim 10 wherein said baseplate has an inferior surface including a pair of inferiorly extending receptacles for receiving an end portion of each of said first and second fins.

12. The modular tibial implant as set forth in claim 11 wherein each receptacle has a female tapered portion for engaging a male tapered portion on said first and second fin end portions.

13. The modular tibial implant as set forth in claim 8 further comprising a polymeric insert for placement on said baseplate having a superior bearing surface and an inferior surface for engaging a superior surface of said baseplate and having an opening on an inferior surface sized to receive said means for coupling said bone engaging element upon placement of said insert on said baseplate.

14. The modular tibial implant as set forth in claim 8 wherein said bone engaging element is a finned keel.

15. A method for coupling a bone engaging element to a tibial baseplate comprising:

resecting the proximal tibia to form a planar surface;

implanting a bone engaging stem element in the prepared proximal tibia, the stem having a proximal coupling element having a dovetail shape;

placing a tibial baseplate having an opening therein for receiving said proximal coupling element on said bone engaging stem element; and inserting a dovetail shaped locking element into engagement with said proximal coupling element to lock said bone engaging element to said baseplate wherein said locking element is inserted in a direction generally parallel to said planar surface.

16. The method as set forth in claim 15 wherein said locking element is inserted in a generally anterior-medial or anterior-lateral direction.

* * * * *